United States Patent [19]

Rose

[11] Patent Number: 4,945,928

[45] Date of Patent: Aug. 7, 1990

[54] SMOKING OF REGENERATED TOBACCO SMOKE

[76] Inventor: Jed E. Rose, 1371 Appleton Way, Venice, Calif. 90291

[21] Appl. No.: 322,689

[22] Filed: Mar. 13, 1989

Related U.S. Application Data

[63] Continuation-in-part of Ser. No. 840,072, Mar. 17, 1986, Pat. No. 4,846,199.

[51] Int. Cl.$^5$ ............................................. A24F 47/00
[52] U.S. Cl. ..................................... 131/270; 131/273
[58] Field of Search ............... 131/173, 270, 194, 359, 131/369

[56] References Cited

U.S. PATENT DOCUMENTS

1,826,331 10/1931 Traube ................................. 131/173
3,508,558 4/1970 Seyburn ................................ 131/173

Primary Examiner—V. Millin
Attorney, Agent, or Firm—Robert J. Schaap

[57] ABSTRACT

A method and apparatus for regenerating tobacco smoke such that certain of the constituents may be smoked upon aerosolization thereof. The method and apparatus relies upon generating smoke from tobacco leaves or other grown plant substances and passing the smoke through a solvent, such as water. Certain of the fluidized components and certain of the gaseous components in the stream of tobacco smoke may then be captured in and preferably dissolved in the solvent. The dissolved or suspended smoke components may then be formed into an aerosol for inhalation by a user. By dissolving selected components in the solvent, many of the harmful gaseous and fluidizided constituents of a smoke stream are eliminated. Moreover, an aerosol is generated such that the particle sizes of the aerosol are sufficiently large that they are predominantly deposited in the upper respiratory tract. In this way, the smoker receives the sensations to which the smoker is normally accustomed from tobacco smoke without many of the harmful side effects of tobacco smoke.

39 Claims, 2 Drawing Sheets

SMOKING OF REGENERATED TOBACCO SMOKE

GOVERNMENT RIGHTS

This invention was made with U.S. government support under Grant No. NIDA DA 02665 awarded by the Department of Health and Human Services; also with the material support of the Veterans Administration. The government has certain rights in this invention.

RELATED APPLICATIONS

This application is a continuation-in-part of my co-pending U.S. patent application Ser. No. 840,072, filed Mar. 17, 1986, entitled "Smoking of Regenerated Tobacco Smoke" (now U.S. Pat. No. 4,846,199).

BACKGROUND OF THE INVENTION

1. Field of the Invention

This invention relates in general to certain new and useful improvements in apparatus and methods for enabling smoking tobacco and other burnable plant substances with substantially reduced health hazards and more particularly, to apparatus and methods which use regenerated tobacco smoke with substantially reduced presence of many of the toxic constituents normally present in tobacco smoke.

2. Brief Description of the Prior Art

In recent years, with the recognition of the harmful effects of tobacco smoking, there have been numerous campaigns and programs by governmental agencies and various health groups and other interested organizations to disseminate information about the adverse health effects resulting from tobacco smoking. Moreover, and as a result of this recognition of the harmful effects, there have been many programs directed to attempts to reduce smoking incidence.

The present successes in achieving reduction in the incidence of smoking have been relatively poor with presently known techniques. The present state of the art involves both behavioral approaches and pharmacological approaches. Approximately 70 percent or more of the tobacco smokers who initially quit smoking after using some behavioral or pharmacological approach to singly reduce smoking incidence, generally relapase and return to the habit of smoking at their former rate of smoking within about a one-year period of time.

The behavioral and psychological approach primarily relies upon behavior modification. There have been several programs which employ reward and punishment techniques to reduce the desire for smoking. However, as indicated above, these approaches have not proved to be very effective.

Another commonly employed approach to reduce the incidence of tobacco smoking relies on substitute smoking devices. The so-called "low tar and nicotine" cigarette has been offered as a means of providing a safer mode of smoking. However, these cigarettes often suffer from the lack of taste to which the normal smoker is accustomed and notwithstanding, these cigarettes do not eliminate or even reduce many of the harmful gases present in cigarette smoke.

One of the most successful approaches to date in reducing the incidence of smoking relies upon nicotine containing chewing gum which is designed to reduce smoking withdrawal symptoms. The use of the nicotine gum suffers from several problems including not only the bad taste and destruction of dental appliances, but the gastrointestinal upset which results therefrom and which also reduces compliance. In addition, it has been found that the nicotine containing gum does not satisfy the craving that most smokers experience for the distinct sensations in the throat and chest elicited by nicotine in the smoke. Over the course of many years of tobacco smoking, these particular sensations have become an important part of and associated with the habit of smokers and gives rise to tobacco smoke dependency in most of the tobacco smokers.

In view of the fact that the presently available techniques and substitutes for smoking have not sufficiently reduced the number of smokers or at least aided in reducing the incidence of smoking by any particular smoker, recent attention has been directed to finding some substitute which will satisfy the craving of the smoker but which eliminates many of the harmful side effects of smoking. It is also desirable to provide such a substitute which will also have some effect in reducing the incidence of smoking.

There has been recent attention directed to the modification of either the tobacco or of the cigarette in order to reduce some of the direct harmful effects of cigarette smoking, but which will still provide the desired sensory effects. One of the common techniques employed is that of the addition of a filter to a cigarette which serves the function of diluting the smoke stream and/or blocking some of the harmful particulate material, such as several harmful components of tar and the like. To some extent the filter also blocks some of the gaseous constituents. The filtered cigarette has met with a fairly substantial amount of success, although it only has limited effectiveness in reducing the direct harmful effects of tobacco smoke. For example, the filter does not remove many or otherwise substantial quantities of the quite harmful and generally poisonous gases, such as hydrogen cyanide and carbon monoxide which are generated in cigarette smoke.

There has also been some attempt to breed tobacco plants with less carcinogenic constituents. However, this approach has also met with limited success. At present there is insufficient technology or knowledge to selectively and efficiently breed the tobacco without the harmful constituents. Notwithstanding, even with inherent generation of some of the harmful gases such as carbon monoxide and possibly hydrogen cyanide upon combustion of tobacco leaves.

There is a non-combustible cigarette which delivers nicotine vapors, presently under development. It was theorized that the delivery of nicotine and a sustaining of a certain level of nicotine in the blood stream of the individual would satisfy the nicotine craving of the smoker. However, this proposed nicotine vapor cigarette has many shortcomings in that the vapor delivery system does not deliver nicotine to the same region of the respiratory tract as with an aerosol, such as in the cigarette smoke. As a result, there is an excess of taste of nicotine in the mouth which is quite undesirable. The aroma also differs substantially from that of a conventional cigarette. A method of generating smoke by heating rather than burning tobacco extracts has also been described in European Patent Application No.86 109589.1 filed July 14, 1986, by R. J. Reynolds Tobacco Company. However, this method delivers substantial nicotine to the lungs of the user, and hence may maintain nicotine dependency. Also substantial quantities of carbon monoxide may be delivered by this device.

In my aforesaid co-pending parent patent application, there is provided a method and an apparatus for regenerating tobacco smoke and which relies upon the use of condensed tobacco smoke constituents. Prior to this aforesaid co-pending patent application, there has not been any effective means to enable a tobacco smoker to continue with a smoking habit and receive the same sensory pleasure to which the smoker is normally accustomed with the elimination of many of the harmful constituents present in the tobacco smoke. The aforesaid pending parent patent application provided both a method and an apparatus for overcoming that problem. The present invention provides an improvement over the apparatus and the method taught in the aforesaid pending patent application in that it has been found that a greater portion of the smoke constituents, including some of the solid phase constituents, can be eliminated and moreover, particle size regulation can easily be obtained in the aerosol to control the delivery to the upper respiratory tract.

OBJECTS OF THE INVENTION

It is, therefore, one of the primary objects of the present invention to provide a method of regenerating tobacco smoke and which is capable of being smoked without many of the harmful substances normally present in tobacco smoke.

It is another object of the present invention to provide a method of regenerating tobacco smoke and which is capable of being smoked with a substantially reduced percentage of many of the harmful constituents normally present in tobacco smoke.

It is a further object of the present invention to provide a method of regenerating tobacco smoke by passing the smoke through a solvent and thereby separating many of the harmful gaseous and fluidized constituents from other constituents.

It is still a further object of the present invention to provide an apparatus for regenerating tobacco smoke by using a solvent extraction technique to thereby separate many of the harmful constituents from other gaseous and fluidized constituents normally contained in a stream of tobacco smoke and which enables a smoking of these solvent extracted constituents upon aerosolization thereof.

It is an additional object of the present invention to provide a method of smoking constituents of tobacco smoke with the same sensory effects normally provided by tobacco smoke but without many of the harmful constituents normally included in tobacco smoke.

It is another salient object of the present invention to provide a two step process of combusting tobacco smoke and collecting certain constituents thereof and thereafter smoking an aerosol containing such constituents.

It is still another object of the present invention to provide a method for reducing the incidence of tobacco smoking by providing a tobacco smoke substitute.

With the above and other objects in view, my invention resides in the novel features of form, construction, arrangement and combination of steps in the method and apparatus hereinafter described.

BRIEF SUMMARY OF THE DISCLOSURE

This invention relates in a broad aspect to a method and apparatus for providing a substitute for normal tobacco smoke as well as a method for reducing the incidence of tobacco smoking. This substitute relies upon a regenerated tobacco smoke. The regenerated smoke is far less harmful to the smoker than the normal tobacco smoke but can still provide many, if not most of the respiratory tract sensations to which the smoker has become accustomed.

In my aforesaid co-pending parent patent application, there is provided both a method and an apparatus which utilizes a formation of an aerosol of condensed tobacco smoke constituents. In that case, many of the harmful gaseous components, such as carbon monoxide and the like, were eliminated and the fluidized constituents were condensed. The fluidized condensed constituents were thereafter aerosolized for smoking. In this way, the smoker still obtained the normal respiratory tract sensations achieved from tobacco smoke with a reduced concentration of nicotine. More importantly, many of the very harmful constituents, such as carbon monoxide and the like were eliminated.

The present invention provides an improvement in both the apparatus and the method for producing regenerated tobacco smoke, as well as an improved apparatus and method for utilizing and smoking the regenerated tobacco smoke. It has been found, in accordance with the present invention, that by contacting the stream of tobacco smoke with a solvent, many of the constituents can be entrapped in the solvent, allowing other of the constituents to pass beyond the solvent and to, in effect, be extracted. In this way, there has been an elimination of many of the harmful gaseous constituents, as well as many of the undesirable solid constituents. In a normal tobacco smoke stream, the solid and semi-solid constituents are usually present in a fluidized state and are typically referred to as "fluidized constituents". Thus, the present invention is highly effective in removing a substantial portion of the very harmful gaseous constituents and the fluidized constituents. Even moreso, the present invention can be used in such manner so as to deliver only a reduced percentage of the solvent extracted fluidized constituents and gaseous constituents to the smoker.

It is well established that tobacco smoke and smoke from other plant substances contain a large number of gaseous constituents, many of which are poisonous. The gaseous constituents in tobacco smoke, contain for example, hydrogen cyanide, ammonia, formaldehyde in a gaseous phase, carbon monoxide and the less harmful carbon dioxide. Water vapor, nitrogen and oxygen are usually also present in the gaseous constituents. Inasmuch as many of these gaseous constituents are highly poisonous, it is desirable to eliminate them from the normal tobacco smoke.

Normal tobacco smoke also contains fluidized components which constitute the visible part of the smoke stream. These fluidized component condensates are typically comprised of small solid particles and liquid particles or droplets. Inasmuch as the fluidized components are present in normal tobacco smoke and operate to form a vapor stream (even though not in a gaseous state), they are often times referred to as "fluidized" constituents. Nevertheless, after the tobacco has been ignited and combusted, after a short period of time the solid and liquid particles do condense to form a condensate. This condensate, a collection of fluidized components, is usually comprised of several tar-like substances.

In accordance with the present invention, it has been found that superior results are obtained when the tobacco smoke is passed through a solvent bath, so that portions of the gaseous and fluidized constituents may be collected in the solvent bath. In this way a very substantial portion of these fluidized constituents and gaseous constituents may be dissolved in the solvent. However, many of these constituents can be merely suspended in the solvent. In either case, the solvent laden tobacco smoke constituents can be used to form an aerosol for smoking.

In a more preferred aspect of the invention, the tobacco smoke is bubbled through the solvent. In this way, there is an intimate contact of the smoke, and particularly the constituents of the smoke, with the solvent. Those constituents which are capable of being entrapped by the solvent will be so entrapped. The remaining constituents, including both the gaseous constituents, and the fluidized and solid and semi-solid constituents, will pass through the solvent without being extracted. These non-solvent entrapped constituents are then expelled. In this way, there is a complete separation of certain of the constituents from other constituents. Those constituents which are entrapped in the solvent are referred to as "solvent extracted constituents".

The solvent extracted constituents may then be used to form an aerosol which is capable of being smoked. Two separate embodiments of using the solvent extracted constituents are employed. In the first embodiment, the solvent, such as water, which is laden with the dissolved constituents, may be used as such, to form an aerosol. Thus, the aerosol is formed with the solvent and the entrapped constituents therein. In another embodiment of the invention, the solvent extracted constituents may be further separated from the solvent, as for example, by condensing those constituents from the solvent. In this way, a secondary condensation takes place, in that the fluidized components are removed from the solvent. Nevertheless, the fluidized components can then be used to form an aerosol for purposes of smoking.

In either of the aforesaid embodiments, the aerosol contains many of the particles normally generated in tobacco smoke and thereby satisfies many of the desired sensory effects which are achieved with normal tobacco smoke. However, many of the harmful ingredients contained in tobacco smoke have been eliminated. Thus, when the aerosol is generated, it may be inhaled in the same manner as normal tobacco smoke.

The present invention is also effective in that it delivers only a very small percentage of the constituents normally present in tobacco smoke to the alveoli. The present invention is unique in that it is possible to generate an aerosol with selected particle sizes such that only a small percentage of the constituents reach the alveoli. Thus, for example, the aerosol may be generated with particle sizes of about two to about ten microns. More preferably, the aerosol may be generated with particle sizes of about three to about five microns. In this way, a much higher portion of the regenerated tobacco smoke constituents will remain in the upper oral cavity and the upper respiratory tract than is the case with cigarette smoke, which has a particle size on the order of 0.5 microns.

The term "smoking" is used to refer to the inhalation or the in-drawing of the aerosol which is generated, although it should be understood that in a strict sense, the aerosol is not smoke, as such, from combusted tobacco.

In one aspect, the present invention includes a method of producing tobacco smoke constituents which are capable of being smoked. One method of generating the tobacco smoke residue is by a selective distillation of tobacco leaves. Other anaerobic techniques may be employed. In a preferred embodiment of the invention, the method of producing tobacco smoke comprises the burning of the tobacco to produce a smoke which is comprised of fluidized components or constituents, e.g. condensed constituents, and the gaseous components or constituents.

The present invention may be broadly described as a method for producing solvent extracted tobacco smoke constituents which are capable of being smoked. The method comprises heating tobacco to produce a tobacco smoke comprised of a mixture of fluidized components and gaseous components. Thereafter, the method involves introducing the mixture of smoke components into a solvent. Certain of the components are entrapped in the solvent, thereby separating the entrapped tobacco smoke components from the other tobacco smoke components. Finally, the method relies upon expelling the non-entrapped smoke components so that an aerosol may be formed with the entrapped smoke components for smoking.

In a preferred embodiment, the method of separating the components comprises the passing of the mixture of the gaseous components and fluidized components into a solvent bath so that certain of the gaseous and fluidized components can become entrapped therein and allowing the remaining gasses and fluidized components to become expelled. In this way, an aerosol may be formed from the entrapped components.

The present invention also provides an apparatus for producing solvent extracted tobacco smoke constituents which are capable of being smoked upon generating an aerosol thereof. This apparatus comprises a means for receiving a source of tobacco smoke which is capable of being combusted to produce the tobacco smoke. A chamber temporarily receives and holds the tobacco smoke. A liquid solvent is located in this chamber to receive the tobacco smoke and entraps certain gaseous constituents and fluidized constituents in the smoke from the other constituents. An exhaust member is provided for discharging the constituents which have been separated. A container may be provided for collecting the solvent extracted constituents.

In still another aspect, the present invention comprises a method of smoking reconstituted tobacco smoke to provide the sensory effects of normal tobacco smoke without many of the harmful constituents contained therein. This method comprises disposing a container of the solvent extracted components separated from tobacco smoke in relationship to a source of heat. Thereafter, the container is heated to generate a vapor of the solvent extracted constituents when the user thereof desires to inhale smoke. The vapor is passed through a smoke delivery tube upon in-drawing thereof by a smoker to allow receipt in the oral cavity and respiratory tract of the smoker.

The present invention also provides a smoking apparatus to enable the smoking of an aerosol generated from the solvent extracted constituents of tobacco smoke without receiving many of the harmful constituents normally carried in tobacco smoke. This apparatus comprises a housing with a container of the solvent extracted constituents of tobacco smoke located within the housing. A heating means is also located to generate a source of heat in relation to the container to thereby generate an aerosol of the solvent extracted constituents which is capable of being inhaled by a smoker. A tube is associated with the housing to receive the generated aerosol and an outlet end is provided on the tube to be engaged by the smoker so as to receive the generated aerosol in the smoker's mouth and respiratory tract.

This invention possesses many other advantages and has other purposes which will be made more clearly apparent from a consideration of the forms in which it may be embodied. They will now be described in detail for purposes of illustrating the general principles of the invention, but it is to be understood that such detailed descriptions are not to be taken in a limiting sense.

BRIEF DESCRIPTION OF THE DRAWINGS

Having thus described the invention in general terms, reference will now be made to the accompanying drawings in which:

DETAILED DESCRIPTION OF PRACTICAL EMBODIMENTS

Figure 1:
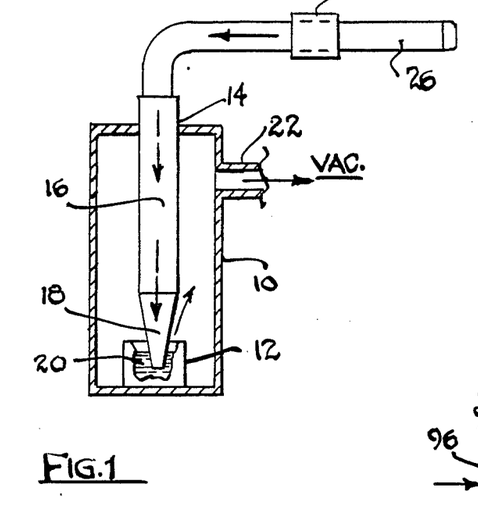
FIG. 1 is a schematic side elevational view, partially in section, of an apparatus for generating solvent extracted tobacco smoke capable of being smoked when in an aerosol form, and which is constructed in accordance with and embodies the present invention.

Referring now in more detail and by reference characters to the drawings, FIG. 1 designates an apparatus for collecting tobacco smoke extract. This apparatus comprises an outer housing 10 with a reservoir or container 12 disposed on the lower wall thereof. The reservoir is provided with a suitable solvent, as hereinafter described in order to extract certain of the constituents in tobacco smoke.

Normal tobacco smoke contains numerous gasses as heretofore described. Moreover, normal tobacco smoke also contains numerous fluidized components which would form solids or semi-solids when condensed. Many of the gasses and fluidized components do not provide for taste or other sensory effects to which the normal smoker has become accustomed, but are quite harmful. As a simple example, carbon monoxide is a primary constituent in tobacco smoke but does not provide taste and, as presently understood, does not contribute to any taste quality or other sensory effect that the normal smoker is accustomed to receive from tobacco smoking. Thus, it is quite desirable to eliminate these gaseous and fluidized constituents.

In accordance with the present invention, by extracting certain of the constituents in tobacco smoke which may include both gaseous constituents and fluidized constituents, and expelling the remaining constituents, the collection of gaseous and fluidized constituents can be aerosolized for smoking. The present invention uses a solvent for extraction of these components. The container or reservoir 12 is therefore provided with a suitable solvent for extracting certain of the components of tobacco smoke.

The upper wall of the housing 10 is provided with an opening 14 to receive an elongate tube 16. The tube 16 has a lower tip portion 18 which terminates below the level of the solvent 20 in the collection reservoir 12. Finally, the housing 10 is provided with a vacuum port 22 for connection to a suitable vacuum source. Connected to the upper and outer end of the tube 16 is an adapter 24 suitably sized and shaped to retain a cigarette 26.

When the cigarette is ignited, a vacuum can be applied to the housing 10 through the vacuum port 22. Inasmuch as the cigarette 26 is in communication with the negative pressure in the housing 10, a continuous draw will be created on the cigarette 26 thereby continuously causing a burning action of the cigarette and pulling smoke generated thereby into the housing 10. Smoke will thereupon travel through the tube 16.

The smoke which is pulled through the tube 16 will be mixed intimately with the solvent 20 in the reservoir 12, inasmuch as it is bubbled through the solvent. Those constituents which are capable of being extracted by and effectively entrapped in the solvent will be effectively removed from the stream of cigarette smoke. The remaining constituents, which are not affected by the solvent, will merely bubble through the solvent and pass through the exit port 22.

It has been recognized that a very substantial portion of the gasses and fluidized components, which are entrapped by the solvent, are actually dissolved in the solvent. This is due to a noticeable orange color which is imparted to the solvent, particularly when the solvent is water, after the tobacco smoke has been bubbled through the water. However, it is believed that certain of the constituents, such as some of the tar particles and the like, may actually be suspended in the solvent.

The solvents may be selected in order to selectively absorb certain of the constituents in cigarette smoke. One of the most preferred solvents is water, inasmuch as it is capable of entrapping certain of the constituents which provide taste and desired sensory effects. However, ethanol, propylene glycol, glycerol and other organic solvents can also be employed. In addition, it is possible to use mixtures of the foregoing, such as mixtures of water and ethanol. Selection of polar and nonpolar solvents will affect those constituents which may be dissolved.

It is also possible to selectively entrap certain of the tobacco smoke constituents by mixing various known solvents. In this way, it is possible to entrap more or lesser amounts of the desired constituents. In addition to the foregoing, it is also possible to adjust the pH of the solvent in order to selectively entrap certain of the constituents and permit other of the constituents to pass through the solvent. Further, temperature may have some effects on the constituents which are selectively extracted in the solvent.

The solvent may also be selected in order to selectively control the entrapment of nicotine. In some cases, it may be desirable to include a low percentage of nicotine and supplement the nicotine by other means. Otherwise, it may be desirable to entrap a higher percentage of the nicotine. Water will entrap a substantial percentage of the nicotine contained in cigarette smoke. In this way, the smoker of the regenerated tobacco smoke will receive at least a portion of the nicotine which the smoker receives through normal tobacco smoking.

As indicated above, it is possible to control the amount of nicotine which is selectively absorbed in the solvent. In this way, it is possible to reduce the amount of nicotine which is selectively absorbed. Selective absorption of the nicotine can be controlled by controlling the pH of the solvent. Thus, the aerosolized solvent can be tailored for particular individuals in order to progressively reduce the nicotine content in the solvent. It is also possible to supplement nicotine in the solvent by administration from other sources, as for example, through the use of a transdermal patch in which nicotine is transdermally administered through the skin of an individual.

The reservoir 12 may be retained as desired so that the contents may be aerosolized at a later date for smoking by the user upon demand. If kept refrigerated or frozen and in the dark, the solvent extracted tobacco smoke constituents can be stored for a relatively long period of time. Nevertheless, when aerosolized, the condensed constituent will form a tobacco vapor stream referred to herein as "smoke" and which is very similar to normal tobacco smoke and approximates both the taste and the appearance of tobacco smoke.

Figure 2:
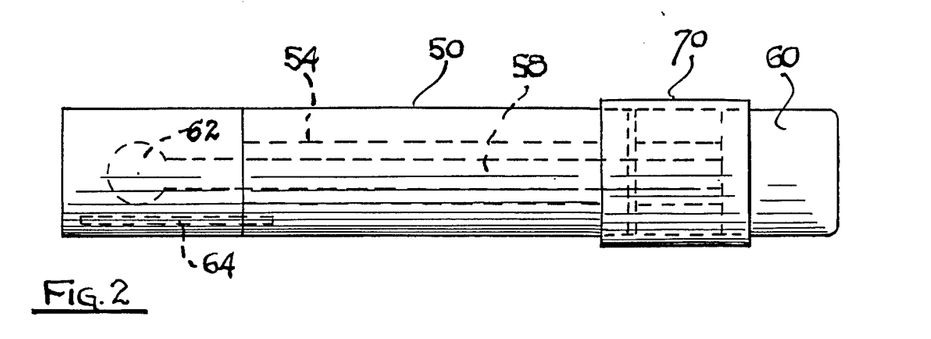
FIG. 2 is a side elevational view of an apparatus capable of being used for smoking solvent extracted tobacco smoke upon forming an aerosol thereof.
Figure 3:
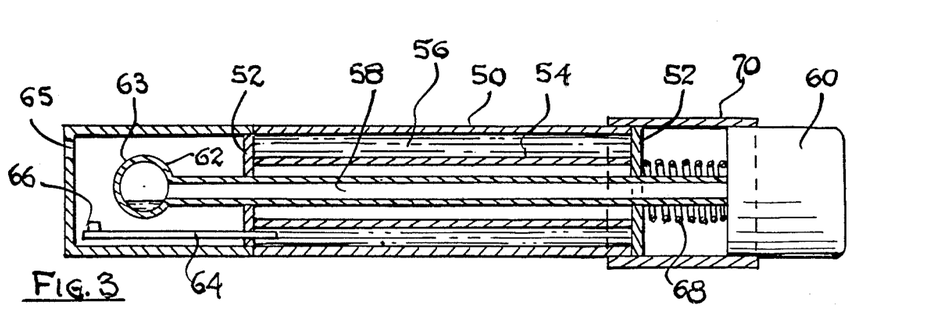
FIG. 3 is a vertical sectional view of the apparatus of FIG. 2.

FIGS. 2 and 3 illustrate one embodiment of an apparatus for smoking an aerosol of the solvent extracted tobacco smoke constituents and comprises an outer housing 50 which may adopt the size and shape of a conventional cigarette. For this purpose, the housing 50 is elongate and cylindrically shaped. Located within the housing 50 is a concentrically disposed, diametrically reduced, cylindrically shaped divider tube 54 which forms an ignitable fluid chamber 56 containing a suitable ignitable fluid, such as a conventional lighter fluid e.g. liquid propane, butane, or the like. Any conventional petroleum distillate, such as conventional lighter fluids may be employed for this purpose.

A pair of intermediate discs or walls 52 and 53 are located within the housing 50. Concentrically disposed within the divider tube 54 is an elongate smoke delivery tube 58. Mounted on the right-hand end of the smoke delivery tube 58, reference being made to FIGS. 2 and 3, is a filter 60 to create a draw or inhalation resistance, such as in a conventional cigarette filter. Located at the opposite end of the smoke delivery tube 58 is an enlarged ampule or reservoir 62 containing the solvent and the entrapped tobacco smoke constituents. The ampule may be formed of glass or graphite or other inert material.

Extending from the chamber containing the ignitable fluid 56 is a wick 64 having an end 66 capable of being ignited to create a flame. However, by reference to FIGS. 2 and 3 it can be observed that the ampule 62 is located in a position where it is not immediately above the flame of the burnable end 66 and therefore is not heated. When the smoker desires to create an aerosol of the condensed constituents in the ampule 62, the smoke delivery tube 58 and hence the ampule 62 are shifted to the left, reference being made to FIGS. 2 and 3. The condensate in the ampule 62 will become heated and form an aerosol.

The ampule 62 may be provided with an air inlet opening 63 so that when a suction is imparted to the ampule 62, through the smoke delivery tube 58, the aerosol will travel through the smoke delivery tube 58 and through the filter 60. A similar opening 65 may be formed in the end wall of the housing 50 for this purpose. The air inlet opening 63 also operates as a vent to prevent excessive pressure build-up within the ampule 62. Thus, when the smoker desires to inhale an aerosolized amount of the solvent extracted tobacco constituents he or she will merely push on the smoke delivery tube 58 so that the ampule 62 is located over the flame of the burnable end 66 and within a matter of a few seconds, a sufficient amount of aerosol has formed, equivalent to that which would be generated in a puff by the smoker on a normal cigarette. The aerosolized constituents which, in effect, form a regenerated tobacco, are visually identical to normal cigarette smoke and provide a similar aroma and other sensory qualities resembling cigarette smoke.

A spring 68 is disposed between the right-hand end wall 52 in the outer housing 50 and the filter 60. Moreover, an outer cover sleeve 70 is disposed over the spring between the filter 60 and the housing 50. The housing 50, as well as the sleeve 70, may both be formed of a suitable paperboard material, which is relatively inexpensive, so that the entire apparatus functions as a disposable cigarette which may be disposed of when the charge of solvent and the extracted smoke constituents in the ampule 62 have been depleted. Otherwise, the entire apparatus of FIGS. 2 and 3 could be constructed to be reusable with the ampule capable of being recharged.

One of the distinct advantages of the smoking apparatus of FIGS. 2 and 3 is that it can be constructed at a relatively inexpensive cost and is highly effective in producing an aerosol of the solvent and the extracted tobacco smoke constituents. Moreover, it is only necessary to boil the solvent and the constituents at a relatively low temperature e.g. about 100 degrees C. As a result, there is no combustion and hence the poisonous products of combustion, as for example, in a normal cigarette, which is combusted at about 800 degrees C., are avoided. In this respect, carbon monoxide is suspected to be one of the main contributors to coronary artery disease and one of the leading causes of death from cigarette smoking. Thus, there is provided a substantial reduction in the risk associated with smoking despite the fact that a small quantity of certain tars, other gasses and nicotine may be delivered to the smoker.

Figure 4:
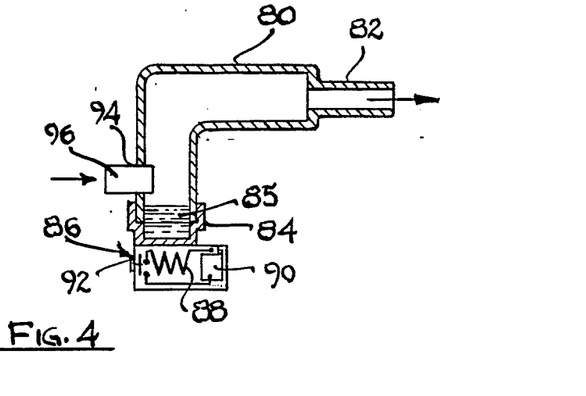
FIG. 4 is a side elevational view, partially in section, of a modified form of apparatus for smoking solvent extracted tobacco smoke and which is also constructed in accordance with and embodies the present invention.

FIG. 4 illustrates still another embodiment of an apparatus for generating a tobacco smoke aerosol which is capable of being smoked. This embodiment of the apparatus comprises an outer housing in the form of an L-shaped tube 80 and which has a reduced end 82 capable of being engaged by the lips of a smoker. Removably secured to the lower end of the vertical leg of the tube 80 is an ampule or reservoir 84 containing a charge of tobacco smoke condensate 85. A heater section 86 is located immediately beneath the ampule 84 and contains a heating coil 88 which may be energized by means of a battery 90. A switch 92 is electrically connected between the battery and the heating coil 88 to cause energization of the heating coil 88, when actuated. In this way, when the heating coil 88 is energized, it will heat a charge of the solvent extracted tobacco smoke constituents thereby causing the generation of an aerosol in the tube housing 80.

The tube housing 80 is also provided with an air inlet aperture 94 containing a conventional cigarette filter 96 located therein. The conventional cigarette filter 96 operates in the same manner as the cigarette filter 60 to create a draw resistance similar to that provided by the filter on a conventional cigarette. Moreover, the filter 96 also serves to preclude the escape of the aerosol through the opening 94. In this way, when the smoker draws on the reduced end 82, the smoker will receive the aerosol of the solvent extracted tobacco smoke constituents much in the same manner as with the apparatus of FIGS. 2 and 3. It should be recognized that in this embodiment of the invention, the apparatus is a non-disposable apparatus such that the ampule can be removed and recharged.

By using a smoke delivery tube of proper length, as for example, the smoke delivery tube 58 or the tube housing 80, it is possible to obtain a selective fractionation of vaporized tobacco smoke constituents. One type of fractionation which is easily achievable in the apparatus of the present invention is a selective distillation of the vaporized constituents. The fraction of the constituents with a higher boiling point will condense first along the length of the smoke delivery tube. The lower boiling point fractions of the constituents which contain a lesser amount of the harmful ingredients will remain in the aerosol to be inhaled by the user thereof.

Another type of selective fractionation which can be achieved to control the composition of the aerosol utilizes the principles of gas-liquid chromatography. By properly coating the interior surface of the smoke delivery tube, it is possible to selectively absorb certain fractions of the aerosolized constituents. For example, by coating the smoke delivery tube with a paraffin, the components with a high affinity for the paraffin will collect on the wall of the smoke delivery tube thereby leaving only the other components for delivery to the smoker.

Inasmuch as the solvent forms part of the aerosolized constituents, that solvent can be selected in order to control the amount of aerosolization. Particularly, selected alcohols forming part of the solvent can affect the boiling point which will affect the temperature of the vapor and hence the condensation of the tobacco smoke constituents on the wall of the smoke delivery tube. In this way, it is possible to control the fraction of the solvent extracted constituents which are delivered to the smoker.

The selective distillation which inherently occurs with a longer length of smoke delivery tube has been found to be highly beneficial in that some of the smokers of the tobacco smoke constituents initially complained of a somewhat "burnt" taste. However, by the selective distillation process, it was found that the undesirable taste was associated with constituents of certain boiling points. Inasmuch as these constituents may deposit along the length of the smoke delivery tube, the sensations and effects achieved by the smoker very closely approximate those achieved with a normal cigarette. Thus, the invention has been found to be highly effective as an alternate source of tobacco smoke without many of the harmful constituents normally found in tobacco smoke.

Figure 5:
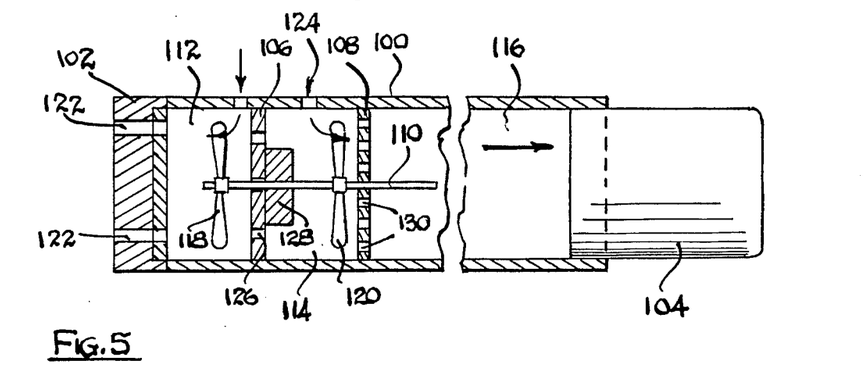
FIG. 5 is a schematic side elevational view, partially in section, and showing another modified form of apparatus for smoking solvent extracted tobacco smoke and which is also constructed in accordance with and embodies the present invention.

FIG. 5 illustrates another modified form of an apparatus for smoking solvent extracted tobacco smoke constituents and which comprises an elongate hollow tube 100. A carbon plug or similar heating element 102 may be located at one end of the tubular housing 100. In this case, the carbon plug can be energized for heating electrically, or by any other form of suitable heating means. The opposite end of the tubular housing 100 is provided with a suitable mouthpiece 104 for the user to engage and create a suction through the tube 100.

A pair of partitions 106 and 108 are located within the tube 100 intermediate its ends. A shaft 110 is journalled in and supported by the partitions 106 and 108. These partitions form a chamber 112 between the carbon plug 102 and the partition 106. In like manner, the partitions 106 and 108 form an intermediate chamber 114. The mouthpiece 104 and the partition 108 form an end chamber 116.

Located within the chamber 112 on the shaft 110 is a first fan blade 118. In like manner, located on the shaft 110 in the chamber 114 is a second fan blade 120. The pitch of the two fan blades 118 and 120 are reversed so as to cause air movement in opposite directions.

The plug 102 is provided with a plurality of openings 122. In like manner, the tube 100 is provided with an opening 124 communicating with the chamber 114. A plurality of openings 126 also extend through the partition 106. In this way, when the user of the smoking apparatus draws on the mouthpiece 104 and creates a vacuum, air will be drawn through the opening 124 into the chamber 114 and into the chamber 112. This will cause a movement of air through the openings 122 and thereby provide an air movement for maintaining a heating of the carbon mass 102.

A porous plug or similar member 128 is located within the chamber 114. This plug may be entrained with the solvent and the extracted tobacco smoke constituents. Moreover, the plug 128 is constructed so that air movement through the plug will easily aerosolize the solvent and the solvent extracted tobacco smoke constituents therein. Moreover, a portion of the tube 100 and perhaps the partition 116 could be formed of a metal to conduct heat from the heating element 102 to the plug 128 thereby further aiding in the formation of an aerosol.

A plurality of similar openings 130 are formed in the partition 108. In this way, when the user draws upon the smoking apparatus, air will move through the opening 124 and into the chamber 114. This will cause an aerosol of some of the constituents in the plug 128. The aerosol is then carried through the openings 130 in the partition 108 and through the mouthpiece 104 to the user.

This type of smoking apparatus can be highly effective in delivering solvent extracted smoke constituents as a regenerated form of tobacco smoke without the delivery of substantial amounts of carbon monoxide and other harmful gases of combustion. Moreover, it can be easily constructed at a low cost.

It is also possible to generate an aerosol without the necessity of heat to boil the solvent and the constituents. This is due to the fact that the solvent may contain, or may be water, or a suitable alcohol, such as ethanol, or the like. If desired, the solvent extracted constituents, even in the solvent, can be added to an additional carrier, such as ethanol, or the like. Generally, about one percent to about ten percent of the solvent extracted constituents should be present in about 90 percent to about 99 percent by weight of alcohol or other carrier. In this way, the carrier and the solvent, along with the solvent extracted constituents, are nebulized, as with an ultrasonic nebulizer.

The aforesaid embodiments of forming an aerosol of the tobacco smoke constituents have generally described the aerosolization of the solvent with the constituents carried therein. This is an effective way of forming an aerosol since the water, or other solvent, along with the constituents entrained therein can easily be aerosolized. However, it may be desirable to further condense the constituents in the solvent in a type of secondary condensation. Thus, for example, the solvent with the extracted tobacco smoke constituents, could be freeze-dried or otherwise treated in such manner as to have the solvent removed. The remaining solvent extracted particles are then available for smoking without the solvent.

Typically, when the solvent has been extracted, the remaining particles may form a lump or heavy mass. This mass may be suitably ground in order to form small particles such as dust-like particles. In this way, the particles may be easily formed into an aerosol for inhalation.

As indicated above, the aerosol of the solvent extracted smoke constituents may be formed by a suitable nebulizer. Any conventional nebulizer may be used to form the aerosol in accordance with the present invention. Further, the solvent extracted constituents may be added to any of those liquid carriers normally employed in aerosol containers. For example, some of the liquid carriers which may be used are the same as those employed in inhalers, as for example, bronchial dilators. The liquid carrier should be relatively inert so that it does not react with the condensate.

Figure 6:
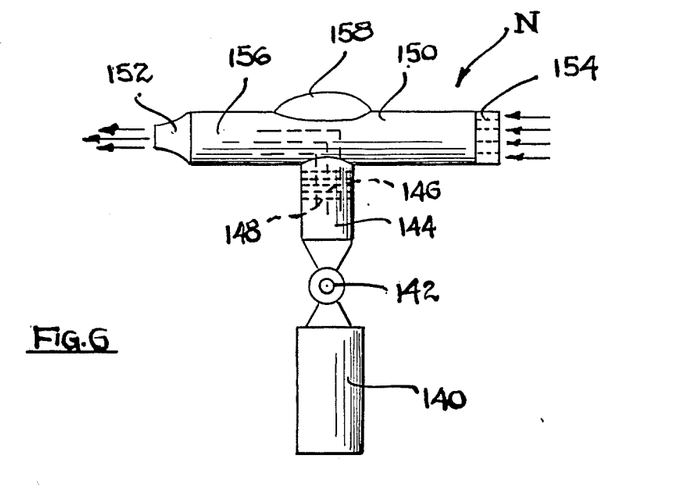
FIG. 6 is a schematic side elevational view of an apparatus for forming an aerosol in accordance with the present invention.

In a preferred embodiment, as hereinafter described, the aerosol is liquid based and is in the form of a spray which may be dispensed from a nebulizer N, as shown in FIG. 6. The nebulizer generally comprises a container such as bottle 140 containing a solution of the solvent and the extracted smoke constituents.

Located at the upper end of the container 140 is a valve 142, which may be in the form of a push-button valve or one with a rotatable valve core capable of being manually manipulated by a user, such that the solvent and constituents can be dispensed from the container upon opening of the valve 142.

Located above the valve is a housing 144 having a plurality of internally located baffles 146. Each of these baffles 146 would have apertures 148 contained therein which control the size of the vehicle droplets. The upper end of the housing 144 is connected to and in fluid communication with an inhalation tube 150 which has a reduced end 152 for introduction into a user's mouth. The opposite end of the tube 150 may have a screen 154 over the open end thereof in order to strain and remove any foreign particles from an entering air stream.

The tube 150 has an internal chamber 156 which is designed to receive a charge of the aerosol spray. The tube 150 may also be provided with an enlarged hump 158 as shown in order to increase the overall size thereof and to insure that the content of the solvent containing smoke constituents (which may be in vapor form) within the tube is sufficient to constitute one full inhalation.

The bottle 140 is preferably a pressurized bottle containing an inert gas under pressure. Various inert gases, such as Freon, or the like, which are normally found in containers of this type, may be employed.

The screen 154 may take the form of a resistive member which somewhat restricts the flow of air therethrough. In this way, the screen can act as a cigarette filter which creates a draw resistance, much in the same manner as one experiences when drawing air through a cigarette. For that matter, a conventional cigarette filter could be fitted upon the right-hand end of the tube 150.

It is known that the size of the aerosol particles will affect the portion of the respiratory tract to which the particles are delivered. The smaller sized particles will migrate to the lower respiratory tract and the larger sized particles will remain in the oral cavity and in the upper respiratory tract. In addition, it is also known that one of the pleasures achieved by the normal smoker, in addition to taste, is the so-called "scratching sensation" experienced by the smoker when the smoke passes through the respiratory tract.

By controlling the size of the aerosol particles, it is also possible to control the areas of the respiratory tract to which the aerosolized condensate may be delivered. It is possible to use particles within the size range of about two microns to about ten microns in accordance with the present invention. It is known that the larger particles will remain in the oral cavity and the upper respiratory tract. The smaller particles below two microns, such as for example 0.5 microns to about one micron will migrate to the lower respiratory tract and to the lungs. Thus, in accordance with the present invention, the aerosol is constructed so as to generate particle sizes within the range of two microns to about ten microns. More preferably, particle sizes in the range of about three microns to about five microns should be generated.

In normal tobacco smoke, a large percentage of the particles have a size range of less than one micron. Accordingly, many of these particles pass directly to the alveoli of the lungs and do not contribute to the taste quality or other sensory effects in the trachea normally obtained from cigarette smoke. It is established that the cigarette smoker has become accustomed to these light irritating sensations and attributes part of the enjoyment of smoking to the scratching effect of the smoke particles in the respiratory tract. However, the smaller particles effectively do not contribute at all to these desired effects and deliver the very harmful constituents directly to the lungs. Although nicotine delivery to the lungs is an effect sought by tobacco smokers, it is not necessary for producing an immediate reduction in the craving for cigarettes.

In accordance with the present invention, and by selecting the proper particle size, it is possible to deliver only a small percentage of the harmful ingredients to the lungs of the individual and thereby maintain a sensory effect and taste quite similar to that obtained from normal tobacco smoking. In this way, it is possible to simulate the conditions of smoking to which the smoker has become accustomed with normal tobacco smoke.

By using a proper mix of the larger sized particles and the smaller sized particles, the latter will penetrate to the lower respiratory tract thereby providing some of the physical stimulation to which the smoker is normally accustomed with conventional cigarette smoke.

The aerosolized condensate particles obtained in accordance with the present invention usually are within the range of about one to about ten microns. It is possible to control the aerosol particle size by adding solvents of known boiling points.

One important aspect which can be achieved by using the reconstituted smoke of the present invention is the fact that the content of nicotine can be reduced in the solvent extracted constituents and even completely eliminated, while maintaining the sensory characteristics of smoke. In conventional cigarette smoke, it is virtually impossible to maintain the sensory qualities of smoke when the nicotine content is markedly reduced. In the present invention, it is relatively easy and simple matter to remove the nicotine, while adjusting the aerosol particle size to compensate for the reduced sensory stimulation of the upper airways. In this way, and as indicated above, the smoker could be provided with solvent extracted tobacco smoke constituents over a period of time which have progressively lesser amounts of nicotine, but larger particle sizes, in order to reduce nicotine dependency.

The composition of the aerosolized smoke constituents in the aerosol could be varied by adjusting the temperature thereof. Higher temperatures would deliver more nicotine in view of the fact that nicotine has a relatively high boiling point and hence a lower vapor pressure at a given temperature than many of the other smoke constituents. Thus, if the solvent, when present, and the solvent extracted constituents were subjected to a prolonged heating at a low temperature most of the more volatile components would be vaporized. A higher temperature vaporization thereof would cause smoke of specific constituents and which would be rich in the less volatile components.

It is also possible to add various components to the solvent extracted constituents from the tobacco smoke. For example, nicotine could be added in order to provide for a higher nicotine concentration delivery to the smoker. In like manner, sweeteners or other ingredients could be added to the ampule in order to alter the composition of the aerosol which is ultimately delivered to the smoker.

The composition of the solvent extracted constituents can also be altered by using chemical extracting procedures in order to remove known or suspected hazardous substances. Thus, a wide range of smoke compositions can be obtained and which would be free of many of the hazardous combustion products, and when using the extraction procedures mentioned above, the constituents could be freed of many of the remaining hazardous constituents. As an example, the solvent extracted tobacco smoke constituents could be treated with ether and two normal sulfuric acid solutions and then fractionated with sodium bicarbonate and sodium hydroxide solutions. The residue would then be fractionated in a silicon gel column and washed with n-hexane to remove a large number of the known carcinogenic substances. This treatment, as well as others which may be employed, are described in Tobacco and Tobacco Smoke, Studies in Experimental Carcinogenesis, by Ernest L. Winder et al, Academic Press, 1967.

It can be observed that one of the significant advantages of the smoking of the regenerated tobacco smoke over current smoking practices is the elimination of the numerous poisonous combustion products normally present in tobacco smoke. The resemblance to conventional smoke coupled with the reduction in risk provide the present invention with a considerable advantage over low tar and nicotine cigarettes.

Another one of the distinct advantages of the smoking apparatus of the present invention is that it effectively eliminates the so-called "side stream" smoke, that is, smoke which is generated by a burning cigarette even when the smoker is not smoking that cigarette. In this case, there is no generation of smoke from the smoking apparatus and the generated smoke is effectively inhaled only by the user thereof.

EXAMPLES

The invention is further illustrated by, but not limited to the following examples.

EXAMPLE 1

A double blind test was conducted with 12 subjects in order to determine the effectiveness of the smoking apparatus and method of the present invention which uses regenerated tobacco smoke. In this case, all 12 subjects were given puffs of smoke from a conventional Marlboro cigarette which delivers about 1.0 milligram of nicotine per each cigarette. These 12 subjects were also given ten puffs of smoke from a nebulizer having the solvent extracted tobacco smoke in accordance with the present invention.

To generate the solvent extracted smoker, a vacuum device was connected successively to five cigarettes, which were combusted with the smoke being drawn through ten cc of distilled water. This smoke solution was then introduced into an ultrasonic nebulizer.

In order to ensure an accurate volume of aerosol in each puff, a specialized apparatus was constructed. The specialized apparatus ensured a constant and controlled amount of smoke to be inhaled by each smoker, regardless of the smoker's own customary puff characteristics. Thus, the apparatus which regulated the volume of air drawn into the cigarette or into the nebulizer with each puff was constructed such than an accurate and constant and maximum value of tar and nicotine were delivered in each, regardless of the smokers usual puff volume intake.

The controlled puff delivery system include two major sections. The first section was comprised of a syringe barrel which served as a hollow plastic cylinder and enclosed a conventional cigarette such as the Marlboro cigarette. This cigarette was inserted into a holder mounted on the inner end of a stopper which sealed the opening of the tube. Three metal rods surrounded this cigarette and were inserted into the inner surface of the rubber stopper. These metal rods were also fused to a metal ring at the distal end of the cigarette and served to guide the lighted cigarette into the barrel just before a puff. A short length of plastic tubing and a mouth piece were connected to the outer end of the stopper.

A glass syringe with a plunger served as an air reservoir. The syringe was connected to the plastic cylinder with Tygon tubing. A three-way valve was connected to the tubing and allowed air to be drawn into the glass syringe before each puff. During each puff, the valve position was changed so that air from the syringe would flow into the plastic cylinder when a subject puffed on the mouthpiece. In this way, it was possible to provide an accurate and constant maximum value of air forming each puff.

In operating this apparatus, the cigarette was first placed into the cigarette holder and lighted. The glass syringe was pulled back to the desired puff volume. Just before each puff, the rubber stopper with the cigarette was quickly inserted into the plastic cylinder. The subject then took a puff from the mouthpiece. During this puff, the syringe plunger in the reservoir was pulled inwardly and supplied a measured quantity of air was drawn into the burning cigarette. The amount of volume in each case was established to be 35 cc per puff.

For the purpose of measuring the effects of the aerosol, each subject was provided with a nebulizer of the aforesaid type. These nebulizers also formed part of the apparatus designed to insure a constant volume in each puff. The controlled puff delivery system for the aerosol of regenerated tobacco smoke included a glass syringe serving as an air reservoir. This syringe was connected to the input valve of the ultrasonic nebulizer. A plastic mouthpiece was attached to the upper baffle of the nebulizer. Beyond this, the mode of operation was similar to that used in delivering a controlled quantity of air to the cigarette except that the cigarette was not used.

In each case, the subjects were not able to observe the type of smoke which was being delivered. An opaque screen was placed in front of the delivery system and the aerosol delivery system. Thus, the user could only observe the plastic tube and the mouthpiece on the end of the plastic tube.

Each of the subjects was randomly given four puffs on the Marlboro cigarette and four puffs on the nebulizer. Each of the subjects were then requested to rate the estimated delivery of nicotine, the strength of the puff and the throat sensation after each individual puff. All of the ratings of each individual were then averaged. Moreover, all of the test subjects were averaged and the results are presented in the graph of FIG. 7.

Figure 7:
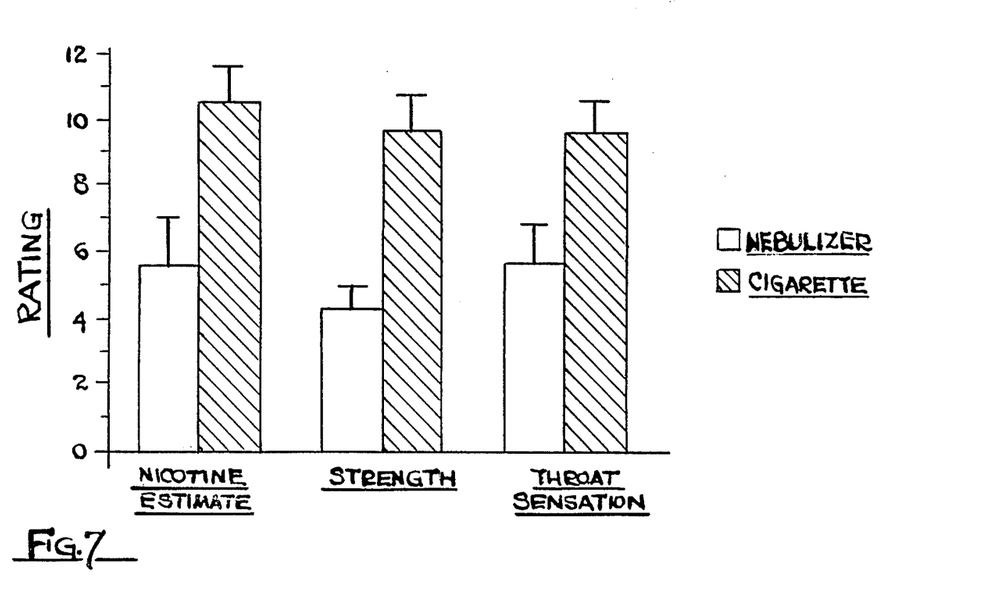
FIG. 7 is a graph showing a ranking by several smokers of similarity and differences between tobacco smoke and the solvent extracted tobacco smoke.

FIG. 7 of the drawings illustrates a rating scale from 0 to 12 which is essentially an arbitrary scale. Moreover, the hatching for each of the bars shown in the chart defines the cigarette smoke and the non-hatched bars show regenerated smoke from the nebulizer. It can be observed that the subjects on an average, estimated that the nicotine concentration was at least half of that of the conventional Marlboro cigarette. In actuality, the nicotine delivery was approximately five percent of that in the Marlboro cigarette as opposed to the estimated 50 percent. In addition, the subjects estimated the strength of the regenerated tobacco smoke to be about half of that of the conventional tobacco smoke. Finally, each of the subjects estimated that the throat sensation was greater than 50 percent of that obtained with the Marlboro cigarette. This is primarily due to the fact that a large portion of the aerosol particles were deposited in the upper respiratory tract.

The nebulizer employed was that offered by Group Technologies, Inc. of Santa Barbara, California under the mark Micron-1.

EXAMPLE 2

A double blind study was conducted using five people in one group who were provided with a nebulizer containing a placebo and eight people in another group who were provided with nebulizers containing solvent extracted tobacco smoke.

In this example, the solvent extracted tobacco smoke was produced essentially in the same way as it was produced in Example 1.

However, in this example, the smoke was bubbled through a 0.9 percent saline solution as opposed to distilled water. The placebo given to each of the five parties in the first group only contained the same 0.9 percent normal saline solution.

A "Micron-1" ultrasonic nebulizer made by Group Technologies, Inc. of Santa Barbara, California was used in producing the regenerated tobacco smoke in accordance with the present invention. Each party in both groups was provided with such a nebulizer.

Each of the thirteen parties were allowed to take puffs of the aerosol freely over an eight hour period in which they were deprived of cigarettes and were asked to rate the aerosol. The parties in the first group which were given the placebo stated, in effect, that it did not provide any nicotine satisfaction and did not provide any of the other sensory satisfactions they obtained with cigarette smoke. The parties inhaling the regenerated tobacco smoke aerosol reported higher liking of the aerosol ($1.6 \pm 0.94$) versus those parties given the placebo ($0.6 \pm 0.89$), where 4.0 was the highest possible rating. The craving for cigarettes reported by parties using the regenerated smoke was lower than those using the placebo. ($5.0 \pm 1.22$ vs. $6.1 \pm 0.65$) when 9.0 was the highest possible rating.

Other factors affecting each of the subjects, in addition to the rated craving for the cigarettes, were also measured on each of the subjects. These other factors which were measured included the amount of carbon monoxide in the bloodstream, the heart rate, pulse and blood pressure. It is known that pulse and blood pressure increase with the cigarette smoking, as would be expected. No such increase was formed with smoking of the regenerated tobacco smoke. The carbon monoxide level of each of the subjects was measured by having each of the subjects blow into a carbon monoxide nebulizer produced under the mark Ecolyzer by Energetics Science of Hawthorne, New York.

Thus, there has been illustrated and described a unique and novel method and apparatus which enables the smoking of solvent extracted tobacco smoke constituents and which provides most of the normal sensory effects achieved with normal tobacco smoke but which also eliminates many of the hazardous constituents. The present invention thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations, and other uses and application which do not depart from the spirit and scope of the invention are deemed to be covered by the invention.

Having thus desccribed the invention, what I desire to claim and secure by letters patent is:

1. A method for producing solvent extracted tobacco smoke constituents and which constituents are capable of being formed into an aerosol for smoking thereof, said method comprising:
  (a) heating tobacco to produce a tobacco smoke comprised of a mixture of fluidized components and gaseous components,
  (b) introducing the mixture of smoke components into a solvent,
  (c) entrapping certain of the components in the solvent thereby separating the entrapped tobacco smoke components from other tobacco smoke components and in which many of such other tobacco smoke components may be harmful to a user of tobacco smoke,
  (d) expelling the non-entrapped smoke components, and
  (e) collecting the solvent with the entrapped smoke components and without many of those components which may be harmful so that an aerosol may be formed of the entrapped smoke components for smoking thereof.

2. The method of claim 1 further characterized in that the step of entrapping certain of the components comprises dissolving those components in the solvent.

3. The method of claim 1 further characterized in that the step of separating certain of the components comprises passing the mixture of gaseous components and fluidized components through a solvent bath causing certain of the gaseous and fluidized components to become entrapped therein and allowing the remaining gaseous and fluidized components to become expelled.

4. The method of claim 3 further characterized in that the method comprises passing the mixture of smoke components into a water bath.

5. The method of claim 1 further characterized in that the step of burning the tobacco comprises the combustion of tobacco in a cigarette and applying a vacuum to the cigarette to extract the smoke generated thereby.

6. The method of claim 1 further characterized in that the said method comprises further separating the smoke components entrapped in the solvent and forming an aerosol from the entrapped components.

7. The method of claim 1 further characterized in that the said method comprises forming an aerosol of the solvent and the components entrapped therein.

8. An apparatus for producing solvent extracted tobacco smoke constituents capable of being formed into an aerosol for purpose of smoking thereof, said apparatus comprising:
(a) tobacco receiving means for receiving a source of tobacco capable of being rapidly combusted and enabling combustion of the tobacco to produce tobacco smoke,
(b) means for heating the tobacco to a combustion temperature to provide tobacco smoke comprised of gaseous constituents and fluidized constituents,
(c) a chamber located in proximate relation to the tobacco receiving means for receiving and temporarily holding the tobacco smoke,
(d) a liquid solvent located in said chamber to receive the tobacco smoke and entrapping a substantial portion of the fluidized constituents and some of the gaseous constituents in the tobacco smoke and thereby separating the entrapped constituents from the other constituents in the smoke and where many of the constituents which are not entrapped may be harmful to a user of the tobacco smoke,
(e) exhaust means operatively associated with said chamber to permit discharge of the non-entrapped constituents, and
(f) means for collecting the solvent with the entrapped constituents therein whereby the collected and entrapped constituents are capable of being easily aerosolized for smoking upon aerosolization thereof.

9. The apparatus of claim 8 further characterized in that a container is disposed in said chamber to receive and hold the liquid solvent.

10. The apparatus of claim 8 further characterized in that the exhaust means comprises a vacuum port downstream of the separating means for connection to a source of a vacuum to thererby create a vacuum to remove the non-entrapped constituents.

11. The apparatus of claim 8 further characterized in that the tobacco receiving means for receiving the tobacco comprises a tube to hold a cigarette.

12. The apparatus of claim 8 further characterized in that the tobacco receiving means for receiving the tobacco comprises a tray for receiving tobacco for combustion therein and which tray is sized to receive a large charge of the tobacco.

13. A method for smoking an aerosol of solvent extracted tobacco smoke constituents to provide the sensory effects of normal tobacco smoke without receiving many of the harmful constituents normally contained in tobacco smoke, said method comprising:
(a) disposing a container of the solvent extracted tobacco smoke constituents separated from tobacco smoke and locating the solvent extracted constituents in a position where they may be contacted by a relatively inert gas from a source of a relatively inert gas,
(b) contacting the solvent extracted constituents with the relatively inert gas,
(c) generating an aerosol of the solvent extracted tobacco smoke constituents in the relatively inert gas and which aerosol will have an appearance and taste similar to that of normal tobacco smoke, and
(d) permitting the aerosol of the solvent extracted constituents to pass through a smoke delivery tube upon drawing by a smoker to allow receipt of the aerosol by the smoker.

14. The method of claim 13 further characterized in that the aerosol is generated by heating the solvent extracted constituents.

15. The method of claim 14 further characterized in that the method comprises locating the container in a position where it is heated in the presence of the inert gas to aid in the generation of an aerosol of the solvent extracted constituents.

16. The method of claim 15 further characterized in that the method comprises separating the solvent extracted components from the solvent and forming an aerosol of the solvent extracted components.

17. The method of claim 15 further characterized in that the method comprises forming an aerosol of the solvent with the solvent extracted components carried thereby.

18. The method of claim 15 further characterized in that the method comprises forming the aerosol with a particle size such that a large percentage of the solvent extracted components are delivered to the oral cavity and upper respiratory tract when the smoker creates a suction on the smoke delivery tube.

19. The method of claim 18 further characterized in that the method comprises forming an aerosol with particle sizes in the range of about two microns to about ten microns.

20. The method of claim 18 further characterized in that the method comprises forming an aerosol with particle sizes in the range of about three microns to about five microns.

21. A smoking apparatus to enable smoking of an aerosol of solvent extracted tobacco smoke constituents which eliminates many of the harmful constituents normally carried in tobacco smoke and reduces the concentration of such constituents, said apparatus comprising:
(a) a housing,
(b) a container of liquid solvent extracted tobacco smoke constituents located within said housing,
(c) aerosol generating means to convert the liquid into aerosolized particles to thereby generate an aerosol of the solvent extracted constituents which is similar to normal tobacco smoke in taste and appearance and which is capable of being inhaled by a smoker, said aerosol generating means generating particles of a size so that a large portion of the aerosol is deposited in the upper respiratory tract such that only a small percentage of the nicotine and other constituents is required to simulate normal tobacco smoke, (d) a tube associated with said housing to receive the generated aerosol and having a first end connected to the container of constituents, and (e) an outlet end associated with said tube and sized so that a smoker may impart a suction to the tube to receive the generated aerosol.

22. The apparatus of claim 21 further characterized in that the aerosol generating means comprises a heating means to generate a source of heat in relation to the container to thereby cause an aerosol of the solvent extracted constituents.

23. The apparatus of claim 21 further characterized in that an air inlet opening is formed in said housing to enable introduction of air to form the aerosol and to enable drawing of the aerosol through the housing upon applying suction to the tube.

24. The apparatus of claim 22 further characterized in that a filter is associated with said air inlet opening to increase draw resistance.

25. The apparatus of claim 21 further characterized in that said tube has a length sufficient so that selective distillation of the aerosolized condensed constituents will take place therein.

26. The aparatus of claim 21 further characterized in that the container of constituents contains a solvent with the solvent extracted consituents therein.

27. The apparatus of claim 21 further characterized in that the container of constituents contains the solvent extracted constituents which have been condensed from the solvent.

28. The apparatus of claim 21 further characterized in that the aerosol generating means generates an aerosol with particle sizes in the range of about two microns to about ten microns, 29. The apparatus of claim 21 further characterized in that the aerosol generating means generates an aerosol with particle sizes in the range of about three microns to about five microns.

30. A smoking apparatus to enable smoking of an aerosol of solvent extracted tobacco smoke constituents comprising:
(a) an elongate tube,
(b) a source of liquid solvent extracted tobacco smoke constituents connected to one end of said elongate tube, and
(c) aerosol generating means to generate heat adjacent said source of solvent extracted tobacco smoke constituents to generate an aerosol of the constituents without any appreciable combustion of the constituents and which does not contain any appreciable amount of the harmful constituents in normal tobacco smoke but is similar to normal tobacco smoke in taste and appearance and which is capable of being drawn through said elongate tube and inhaled by a smoker, said aerosol generating means generating particles of a size so that a large portion of the aerosol is deposited in the upper respiratory tract such that only a small percentage of the nicotine and other constituents is required to simulate normal tobacco smoke.

31. A smoking apparatus to enable smoking of an aerosol of reconstituted tobacco smoke constituents which eliminates many of the harmful constituents normally carried in tobacco smoke and reduces the concentration of such constituents, said apparatus comprising:
(a) a tubular housing,
(b) heating means at one end of said housing for generating heat to aid in the formation of an aerosol of said reconstituted tobacco smoke constituents,
(c) a first divider forming a first chamber in said housing and having a source of reconstituted tobacco smoke constituents therein,
(d) a second divider forming a second chamber in said housing adjacent said heating means,
(e) means in said first chamber to cause an air flow therethrough when a puff is taken on said housing to cause an aerosolization of the constituents, and
(f) means in said second chamber to cause an air flow therethrough to maintain a heating of said heating means.

32. The apparatus of claim 31 further characterized in that the means to cause an air flow is said first and second chamber are impeller means.

33. The apparatus of claim 31 further characterized in that an air inlet opening is formed in said housing to enable introduction of air to form the aerosol upon taking a puff of said housing.

34. the apparatus of claim 33 further characterized in that air opening are located in each of said divider means.

35. the apparatus of claim 31 further characterized in that the source of reconstituted tobacco smoke is a plug impregnated with the constituents.

36. A method for producing an aerosol of solvent extracted tobacco smoke constituents and which constituents are capable of being formed into an aerosol for smoking thereof, said method comprising:
(a) heating tobacco to produce a tobacco smoke comprised of a mixture of fluidized components and gaseous components,
(b) introducing the mixture of smoke components into a solvent,
(c) entrapping certain of the components in the solvent thereby separating the entrapped tobacco smoke components from other tobacco smoke components,
(d) expelling the non-entrapped smoke components so that an aerosol may be formed of the entrapped smoke components or smoking thereof, and
(e) subsequently forming the entrapped smoke components into an aerosol for smoking.

37. The method of claim 36 further characterized in that the step of separating certain of the components comprises passing the mixture of gaseous component and fluidized components through a solvent bath causing certain of the gaseous and fluidized components to become entrapped therein and allowing the remaining gaseous and fluidized components to become expelled.

38. An apparatus for producing solvent extracted tobacco smoke constituents capable of being formed into an aerosol for purposes of smoking thereof, said apparatus comprising:
(a) tobacco receiving means for receiving a source of tobacco capable of being rapidly combusted and enabling combustion of the tobacco to produce tobacco smoke, (b) a chamber located in proximate relation to the tobacco receiving means for receiving and temporarily holding the tobacco smoke,
(c) a liquid solvent located in said chamber to receive the tobacco smoke and entrapping certain of the constituents in the tobacco smoke and thereby separating the entrapped constituents from the other constituents in the smoke,
(d) exhaust means operatively associated with said chamber to permit discharge of the non-entrapped constituents whereby the collected and entrapped constituents are capable of being easily aerosolized for smoking upon aerosolization thereof, and
(e) means for subsequently forming the entrapped smoke constituents into an aerosol for smoking thereof.

39. The apparatus of claim 38 further characterized in that a container is disposed in said chamber to receive and hold the liquid solvent.

* * * * *